(12) United States Patent
Lee (10) Patent No.: US 7,404,226 B2
(45) Date of Patent: Jul. 29, 2008

(54) ELECTRIC TOOTHBRUSH

(76) Inventor: Soo Woong Lee, 21821 Burbank Blvd., #156, Woodland Hills, CA (US) 91367

( * ) Notice: Subject to any disclaimer, the term of this patent is extended or adjusted under 35 U.S.C. 154(b) by 0 days.

(21) Appl. No.: 11/671,427

(22) Filed: Feb. 5, 2007

(65) Prior Publication Data

US 2007/0124877 A1    Jun. 7, 2007

Related U.S. Application Data

(63) Continuation-in-part of application No. 11/379,862, filed on Apr. 24, 2006, now abandoned.

(60) Provisional application No. 60/596,914, filed on Oct. 28, 2005.

(51) Int. Cl.
*A61C 17/32* (2006.01)
(52) U.S. Cl. .......................... 15/22.2; 15/22.1
(58) Field of Classification Search ............ 15/22.1, 15/22.2, 21.1
See application file for complete search history.

(56) References Cited

U.S. PATENT DOCUMENTS 5,406,664 A * 4/1995 Hukuba ............... 15/22.1
2006/0168744 A1 * 8/2006 Butler et al. ........... 15/22.1

* cited by examiner

*Primary Examiner*—Laura C Guidotti
(74) *Attorney, Agent, or Firm*—Park Law Firm; John K. Park (57) ABSTRACT

An electric toothbrush includes a handle, a brush head with bristles fixed thereto, a reciprocating bar, an actuator that moves the reciprocating bar back and forth, an actuator receiving recess, an engaging device that engages the brush head with the reciprocating bar so that the brush head moves relative to the reciprocating bar in either penetration mode or polishing mode and a selection device that places the engaging device either in the penetration mode or the polishing mode. The reciprocating bar is protruded from the handle and received in the actuator receiving recess. The brush head moves together with the reciprocating bar in the polishing mode. The brush head is free to move relative to the reciprocating bar within a predetermined distance in the penetration mode. The longitudinal axis of the brush head is inclined from the longitudinal axis of the handle with a predetermined angle.

7 Claims, 6 Drawing Sheets

ELECTRIC TOOTHBRUSH

CLAIMING PRIORITY

This application claims the benefit of U.S. Provisional Patent application bearing Ser. No. 60/596,914 filed on Oct. 28, 2005.

RELATED APPLICATION

This application is a continuation-in-part of U.S. patent application Ser. No. 11/379,862 for "Reciprocal Toothbrush" filed on Apr. 24, 2006 now abandoned, the disclosure of which is incorporated by reference as if fully set forth herein.

BACKGROUND OF THE INVENTION

This invention relates to the field of dental hygiene. Many individuals suffer from periodontal disease. The term "periodontal" is generally defined as the area around the tooth. This includes the gum, periodontal membrane and bone tissue holding a tooth in place. If periodontal disease is diagnosed, dental surgery is typically required to correct the gum condition. Following surgery, it is necessary to keep the space, or sulcus, between the teeth and gum free of any food debris. This is critical for successful healing and improving the gum to a healthy condition.

The healing process following periodontal surgery is critical. Typically, immediately following surgery, the sulcus is filled with temporary protective packing for approximately one to two weeks. Gum swelling resulting from surgery has, after this period of time, subsided to the point where tooth brushing can begin. Dental plaque and food debris must thereafter be kept to a minimum in the sulcus for the gums to continue to heal correctly.

Good oral hygiene for gum healing is one of the most effective dental prophylaxes. For this reason, it is critical to obtain an effective penetration of the toothbrush bristle tips into the sulcus.

However, most individuals tend to brush only the prominent tooth surfaces. These surfaces typically do not require brushing and can be adequately cleaned simply by eating fibrous foods such as meats and vegetables.

To properly clean the sulcus, many experts recommend that the bristle tips must reach to the bottom of the sulcus.

Commonly known among dentists is the Bass technique, a method for properly brushing the tooth and sulcus as described in "Glickman's Clinical Periodontology® 1979, pp729-733". The Bass technique is considered by many dental experts as the most efficient tooth brushing technique; yet most people are either not familiar, or simply don't know how to properly perform this brushing technique.

Proper use of the Bass technique requires a portion of the bristle tips to penetrate into the sulcus with movement of the toothbrush with a short back-and-forth motion without dislodging the tip of the bristles from their position within the sulcus.

The proper method for this technique is that a toothbrush is held using a grip at two points on the brush handle. One point would be the midpoint on the backside of the brush handle, which would be pressed with the index finger. The second point would be on the front side of the handle (same side as the bristles), which the gum-line and slight pressure applied on these two points, and when minimal back and forth motion is applied, the toothbrush will be secure enough in the hand of the user to make the bristles penetrate into the small gum spaces. While performing the above procedure, the user must be able to feel the bristles of the toothbrush with his fingers.

The Bass technique could be more efficiently implemented if a user could insert at least a few of the toothbrush bristle tips to the bottom of the sulcus. Unfortunately, the conventional toothbrush has a high density of bristles so that the result is an ineffective use of the bristles. In other words, bristle density prevents bristles from reaching either the base of the sulcus or deep enough between the teeth spaces.

Despite the fact that the Bass technique is the best brushing technique, it only remains theoretical if user does not determine the proper positioning of the bristles by touch and understand that the bristles need to maintain their linear form for proper penetration. If this is not done, most of the time the bristles will contact the surface of the gum or tooth and simply bend, thus altering the position of the bristle tip and unable to penetrate to the base of the sulcus or deep between the space of adjacent teeth. Using the sense of touch properly, the bristles can penetrate into the small spaces.

When bristles are dragged by generated force such as from side-to-side brushing, bristles cannot maintain its straight and rigid form and, the bristle tips cannot lead into the small spaces due to the exaggerated force and motion applied by the user.

Typical toothbrushes are used to sweep their bristles back and forth across the surfaces of tooth and gum in prophylaxis. In other words, the bristles slide over the small spaces between teeth and between the tooth and the adjacent gum. This sliding action actually causes the bristles to pass over plaque and food debris, or can even force such material deeper into the space.

When a toothbrush is used in this conventional manner, the bristle tips are not properly positioned to be inserted into, nor do they have the necessary contact time within the sulcus to effectively remove plaque and food debris.

SUMMARY OF THE INVENTION

The present invention contrives to solve the disadvantages of the prior art.

An objective of the invention is to provide a toothbrush where the bristles are not dragged and that will effectively work along the gingival sulcus.

Another objective of the invention is to provide a toothbrush achieving tooth polishing function by changing the brush axis, thereby changing the direction of movement and function of the bristles.

Still another objective of the invention is to provide a toothbrush where the bristle tips associated with the toothbrush could penetrate deep into the sulcus, contact the base of the gum and not be dislodged during the implementation of short cleaning.

Still another objective of the invention is to provide a toothbrush that incorporates a small bristle tip surface area on the plurality of the bristles for easy penetration of the bristle tips into the sulcus.

Still another objective of the invention is to provide a toothbrush having reciprocal strokes allowing small number of bristles to move freely.

In order to achieve the above objective, the present invention provides an electric toothbrush that includes a handle, a brush head comprising a head body and a plurality of bristles fixed to the head body, a reciprocating bar provided inside the handle, an actuator that moves the reciprocating bar back and forth, an actuator receiving recess provided inside the head body of the brush head, an engaging device that engages the brush head with the reciprocating bar so that the brush head moves relative to the reciprocating bar in either penetration mode or polishing mode and a selection device that places the engaging device either in the penetration mode or the polishing mode. The reciprocating bar is protruded from the handle and received in the actuator receiving recess. The brush head moves together with the reciprocating bar in the polishing mode. The brush head is free to move relative to the reciprocating bar within a predetermined distance in the penetration mode. The longitudinal axis of the brush head is inclined from the longitudinal axis of the handle with a predetermined angle.

The handle comprises a connecting sleeve that is provided on the end of the handle that is adjacent to the brush head. The selection device comprises a selection sleeve that is provided between the handle and the brush head and surrounds the connecting sleeve, a selection protrusion that is provided inside the selection sleeve and a selection groove that is provided on the connecting sleeve and receives the selection protrusion. The selection groove comprises two angularly spaced mode recesses that keep the selection protrusion either in the polishing mode or the penetration mode. The mode recesses are spaced by about 90 degrees.

The electric toothbrush further comprises an elastic cover sleeve that covers the selection sleeve and part of the brush head that is adjacent to the selection sleeve.

The selection sleeve comprises a guide groove and the head body of the brush head comprises a guide bar that is received in the guide groove and moves along the guide groove.

The reciprocating bar comprises a lock recess and a penetration recess. The engaging device comprises a lock element that engages with the lock recess in the polishing mode, and that is allowed to move within the penetration recess. The lock element has a dimension that fits the lock recess. The penetration recess has a dimension that allows movement of the lock element by the predetermined distance of the penetrating mode.

The lock element comprises a circular pin that is positioned perpendicular to the reciprocating bar. The lock recess comprises a lock recess cut portion that is cut into the reciprocating bar perpendicular to the longitudinal axis of the reciprocating bar, two parallel lock recess walls that have quarter circle shape and a flat lock recess bottom that connects the two lock recess walls. The penetration recess comprises a penetration recess cut portion that is cut into the reciprocating bar perpendicular to the longitudinal axis of the reciprocating bar, two parallel penetration recess walls that have quarter circle shape and a flat penetration recess bottom that connects the two penetration recess walls. The lock recess bottom and the penetration recess bottom are in the same plane.

The actuator comprises a motor and an offset cam device. The cam device converts rotational movement of the motor into reciprocal movement of the reciprocating bar.

For sake of discussion the direction of brush head movement will be articulated in an x-y-z plane always in relation to the face the bristle tips point to, where y-axis is always defined as the longitudinal axis of the toothbrush, brush head and reciprocating bar.

The brush head is moved to-and-fro substantially perpendicular to the longitudinal y-axis of the brush head with an emphasis that it moves along the x-plane with the bristle tips pointing in the x-axis, and is moved back and forth parallel to the longitudinal y-axis of the brush head simultaneously in the penetration mode. The brush head is moved side-to-side substantially perpendicular to the longitudinal y-axis of the brush head with an emphasis that it moves along the x-plane with the bristle tips pointing in the z-axis, and is moved back and forth substantially parallel to the longitudinal y-axis of the brush head simultaneously in the polishing mode.

The displacement of parallel movement of the brush head in the penetration mode is smaller than the displacement of the parallel movement of the brush head in the polishing mode.

The parallel movement of the brush head in the penetration mode is caused by friction between the reciprocating bar and the actuator receiving recess. The to-and-fro movement of the brush head in the x-plane in the penetration mode is caused by the inherent oscillatory motion of the reciprocating bar driven through the guide at the open end of the connecting sleeve by the offset cam mechanism.

The parallel y-axis movement, as well as the side to side x-axis movement of the brush head with bristles pointing in the z-axis in the polishing mode follows the movement of the reciprocating bar driven through a guide by an offset cam. In this mode the lock element attached to the brush head is mated to the lock recess in the reciprocating bar and is fixed to move as a singular unit.

The electric toothbrush further comprises an elastic ring that is installed on the open end of the connecting sleeve and contacts the reciprocating bar as it slides through the elastic ring. The predetermined size and density of the elastic ring reduces the vibration of the reciprocating bar controlling the force exerted by the brush head on the subject's tooth and gum.

The present invention introduces an electric toothbrush that uses a brush head having a reduced number of bristles and that provides two bristle head positions for teeth cleaning. The first is a polishing position for polishing the tooth surface. The second is a penetration position where the bristle head is rotated 90 degrees from the polishing position for reciprocal action of the bristles in a direction into and away from contact with the tooth surface. Stated a different way, the bristle head, when in the polishing position, faces the z-axis and travels substantially along the longitudinal y-axis and perpendicular the x-axis of the toothbrush while the bristle head, when in the penetration position, faces the x-axis and travels substantially along the x-plane perpendicular to the longitudinal y-axis of the toothbrush and a slight parallel motion along the longitudinal y-axis.

The penetration position permits the necessary bristle penetration into the sulcus for effective removal of plaque and food debris lodged within the sulcus and spaces between the teeth.

A key feature of the present invention is recognizing that for the penetration position, allowing the bristle tips to move freely longitudinally as much as possible will minimize any exaggerated force imparted by the user while brushing and allow the bristle tips to vertically align with the small spaces, even if momentarily, and work satisfactorily. The reciprocal action that offsets the short back and forth movement is the best possible method for more efficiently displacing the bristle tips into the spaces between tooth and gum.

Another key feature of the invention is that the user does not have to substantially adjust his grip. By simply rotating the brush head, the user can adjust from a penetration mode to the polishing mode and continue to hold the toothbrush substantially the same way for either mode.

However, it should be noted that in the preferred embodiment the brush head is rotated 90 degrees. The theoretical orientation for using the Bass Method is at a 45 degree angle to the long axis of the tooth; however, in practice with the invention, it is not necessary for the user to regrip or rotate the wrist by as much as 45 degrees, but only to rotate or regrip slightly so that the brush tips are at an angle preferably between 65 to 80 degrees to the long axis of the tooth. The reciprocal penetrating action of the invention does not necessitate the full 45 degree angle mentioned for effective penetration into the gum space.

The reciprocal penetration action of my brush complements the Bass technique discussed earlier.

As stated earlier, my electric toothbrush has two brush head positions: one for polishing and the other for penetration cleaning. In my preferred embodiment, in order to change from one setting to the other, the brush head orientation must be changed relative to the base. Changing the orientation permits the user to hold the toothbrush in substantially the same way for polishing as well as for plaque and food debris removal from the sulcus. Preferably, the brush axis is adjustable by 90 degrees in a left or right turn action.

My invention includes brush tips that are designed to more effectively clean the lingual surface of the anterior and posterior teeth of the lower jaw. The density of the bristle-tips making contact upon the tooth and gum was designed to be less dense than conventional toothbrushes, preferably making rows of bristles that collectively taper.

Preliminary Testing

In preliminary testing which preceded the final design, a standard toothbrush was modified. Specifically, the bristle density was reduced as well as the total surface area occupied by bristles. The result is a brush head that is smaller in area than conventional brush heads with a less dense bristle population. However, patients found it difficult to implement the Bass technique for inserting the bristles into the small space between the tooth and gum.

Additionally, the modified toothbrush could function properly only when the integrity and alignment of the bristles for penetrating into the sulcus were maintained in a substantially straight and rigid form during the application of the pressured strokes of the Bass technique.

In order to function properly, the bristle tips must substantially penetrate to the base of the sulcus. Short strokes in a back-and-forth direction combined with slight pressure into the gum-line are then used while the bristle tips are engaging or digging into the gum area located at the base of the sulcus so that the bristle tips do not slide out of or exit from the sulcus.

After completion of the strokes, the brush is first moved horizontally so the tips dislodge, then moved across to an adjacent area and the same procedure is repeated. A more detailed description of this method now follows:

While the intended results were obtained, the required brushing instructions turned out to be difficult to follow.

Based on the difficulties associated with using bristles rigidly affixed to a brush head to clean the spaces between tooth and gum, a toothbrush was designed with a slidable brush head which is to some degree independent of the brushing movement imparted by the user. This new design tends to maintain the bristles in the correct position for penetration into and cleaning of the sulcus more effectively. My new design not only provides an effective cleaning of the space between tooth and gum but also the polishing of tooth surface when the brush head is adjusted 90 degrees.

Improved Toothbrush Design

My toothbrush has two settings: penetration mode and polishing mode.

Penetration Mode

For this setting, the electric toothbrush displaces the bristle head substantially in a direction perpendicular to the longitudinal axis of the toothbrush along the plane the direction the bristles face. Thus, when the toothbrush is held by the user for brushing, the bristles of the brush head reciprocally move into contact with the teeth and gum. However, because of the rapid vibrational movement as well as the holding position of the toothbrush, it is possible that the bristle tips will not align to the minute contours of the tooth and gum, but will move only according to the limited direction the mechanized cam motion allows, thus not effectively penetrate between the teeth or into the sulcus.

For this reason, it is preferable that the penetration mode includes the ability for the bristle head to freely and slidably move a short distance along the longitudinal axis of the toothbrush that follows or conforms to the contours of tooth surface and gum space the bristles contact. When this feature is incorporated into my invention, the bristles, rather than being bendable when contacting the tooth surface, are able to slide longitudinally a short distance to align with the tooth space and thus remain in a substantially straight condition for deeper penetration between the teeth or into the sulcus or the space between adjacent teeth.

The present invention cleans not only the tooth surface and gum spaces but also effectively manages simple gingivitis (minor gum inflammation). Unlike the bristles found on a conventional toothbrush which are dragged across the tooth surface in a back and forth, or up and down motion following only the mechanized motions of either the user or an electric cam device, the reciprocal toothbrush is designed so that an effective number of bristle tips can penetrate into the sulcus.

My electric toothbrush design incorporates bristles that are cut to form ridges to enhance contact in small area and spaces, provide dual function that is reciprocal and polishable, and control interchangeable direction of stroke by twisting the brush neck with a thumb and index finger.

In the penetration mode, the slidable feature diminishes the bristle resistance associated with the tooth surface. As a result, more bristles are available for penetration into the surrounding crevices and spaces, for more effective removal food debris and other substance from the deep spaces of the sulcus by reciprocal action.

Polishing Mode

The brush head stroke is changed from a penetrating or digging motion to a substantially side-to-side or up-and-down motion in one plane perpendicular to the direction the bristles face. To achieve this change, my preferred embodiment requires that the brush head be rotated relative to the base by 90 degrees.

Also, when the brush head is rotated, it simultaneously locks the position of the brush head preventing the sliding movement that was present for the penetration mode.

Brush head movement substantially along the longitudinal axis of the toothbrush, is typical of" conventional electric toothbrushes and is also the case for my invention. Therefore, for the polishing mode, my toothbrush performs the same function as conventional electric toothbrushes.

This direction of stroke can be used to brush in the traditional manner of sweeping and polishing the prominent tooth surfaces.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE INVENTION

Figure 1A:
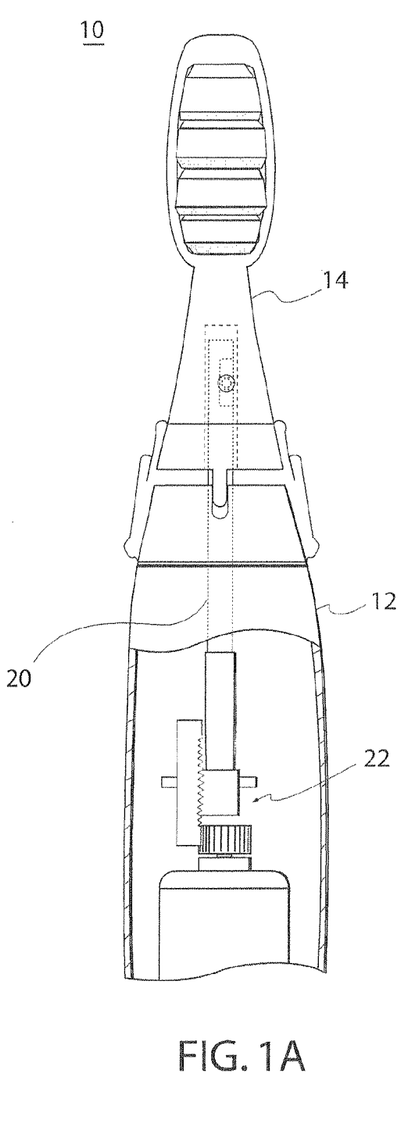
FIG. 1A is a front elevation view showing an electric toothbrush according to the present invention.
Figure 1B:
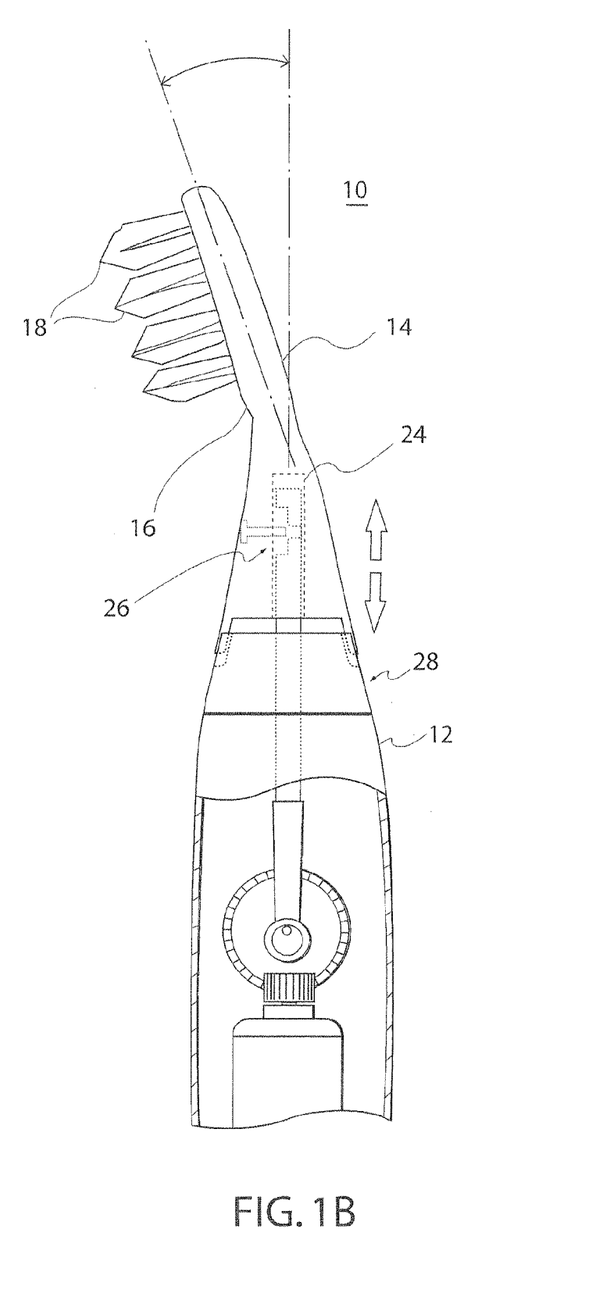
FIG. 1B is a side elevation view showing the electric toothbrush.

FIGS. 1A and 1B show an electric toothbrush 10 that includes a handle 12, a brush head 14 comprising a head body 16 and a plurality of bristles 18 fixed to the head body 16, a reciprocating bar 20 provided inside the handle 12, an actuator 22 that moves the reciprocating bar 20 back and forth, an actuator receiving recess 24 provided inside the head body 16 of the brush head 14, an engaging device 26 that engages the brush head 14 with the reciprocating bar 20 so that the brush head 14 moves relative to the reciprocating bar 20 in either penetration mode or polishing mode and a selection device 28 that places the engaging device 26 either in the penetration mode or the polishing mode.

The reciprocating bar 20 is protruded from the handle 12 and received in the actuator receiving recess 24. The brush head 14 moves together with the reciprocating bar 20 in the polishing mode as shown in FIG. 1B and FIG. 7B.

Figure 7A:
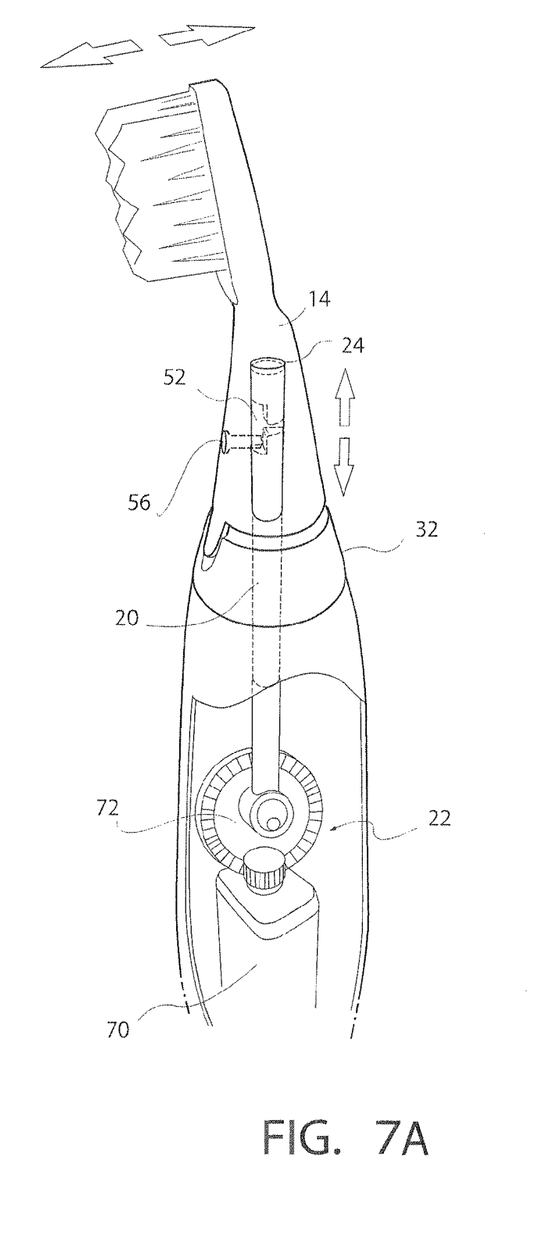
FIG. 7A is a perspective view showing operation of the electric toothbrush in the penetration mode.
Figure 7B:
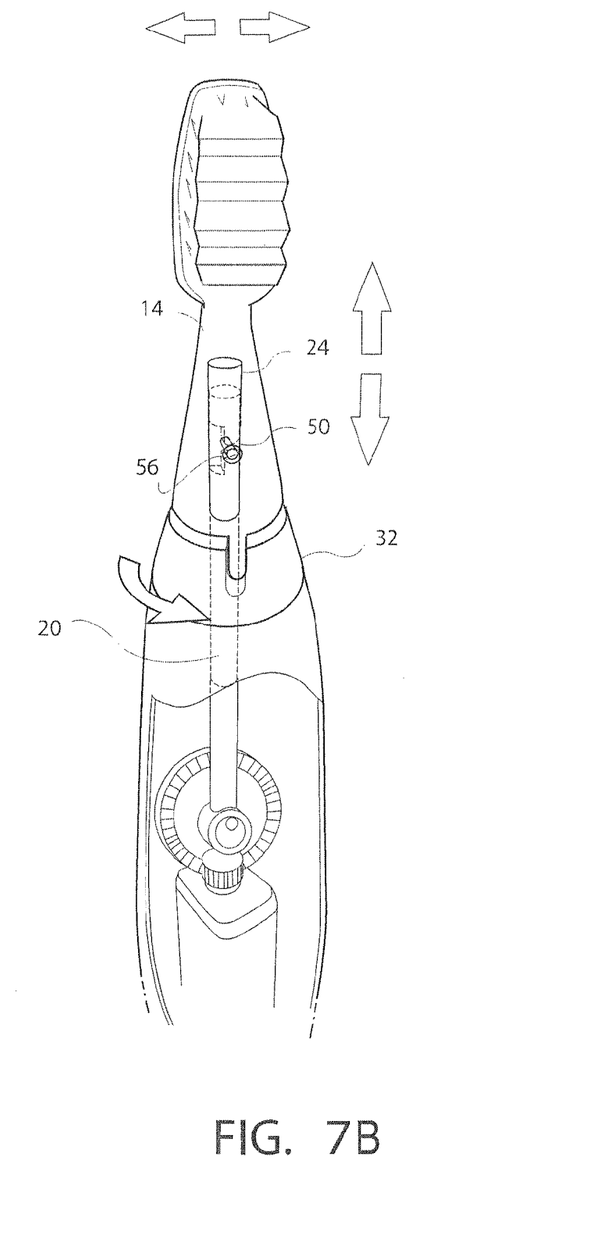
FIG. 7B is a perspective view showing operation of the electric toothbrush in the polishing mode.

The brush head 14 is free to move relative to the reciprocating bar 20 within a predetermined distance in the penetration mode as shown in FIG. 1A and FIG. 7A. As shown well in FIGS. 1B, 2A and 7A, the longitudinal axis of the brush head 14 is inclined from the longitudinal axis of the handle 12 with a predetermined angle.

Figure 3:
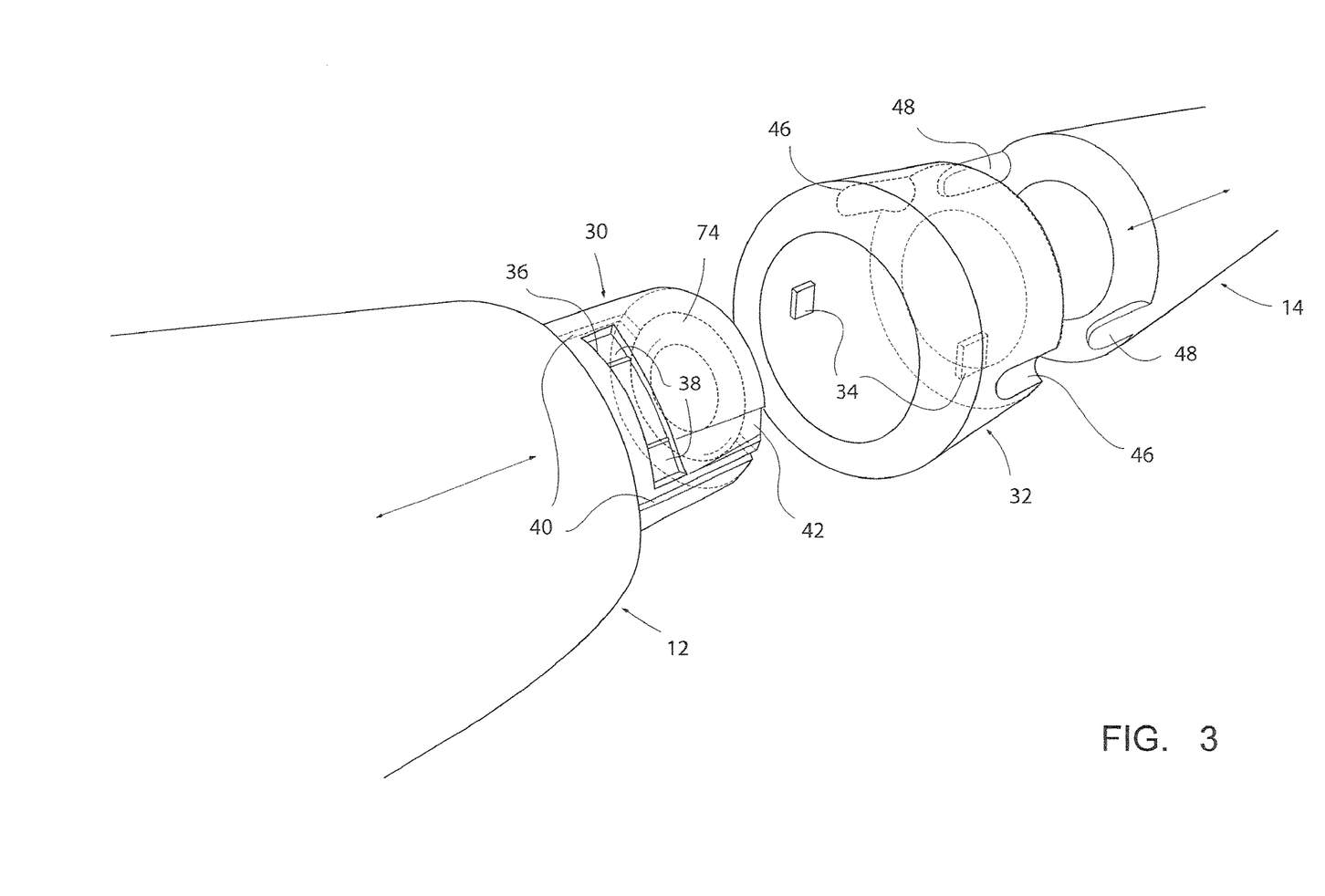
FIG. 3 is a partial exploded view of the electric toothbrush.

FIG. 3 shows that the handle 12 comprises a connecting sleeve 30 that is provided on the end of the handle 12 that is adjacent to the brush head 14. The selection device 28 comprises a selection sleeve 32 that is provided between the handle 12 and the brush head 14, and surrounds the connecting sleeve 30, one or more selection protrusions 34 that are provided inside the selection sleeve 32 and one or more selection grooves 36 that are provided on the connecting sleeve 30 and receive the selection protrusions 34. The selection groove 36 comprises two angularly spaced mode recesses 38 that keep the selection protrusion 34 either in the polishing mode or the penetration mode. The mode recesses 38 are spaced by about 90 degrees. The connecting sleeve 30 also includes conforming grooves 40 that allow the connecting sleeve 30 to accept the selection sleeve 32, and an insertion groove 42 for the selection protrusions 34.

The selection sleeve 32 comprises two guide grooves 46 and the head body 16 of the brush head 14 comprises two guide bars 48 that are received in the guide grooves 46 and move along the guide grooves 46.

Figure 4:
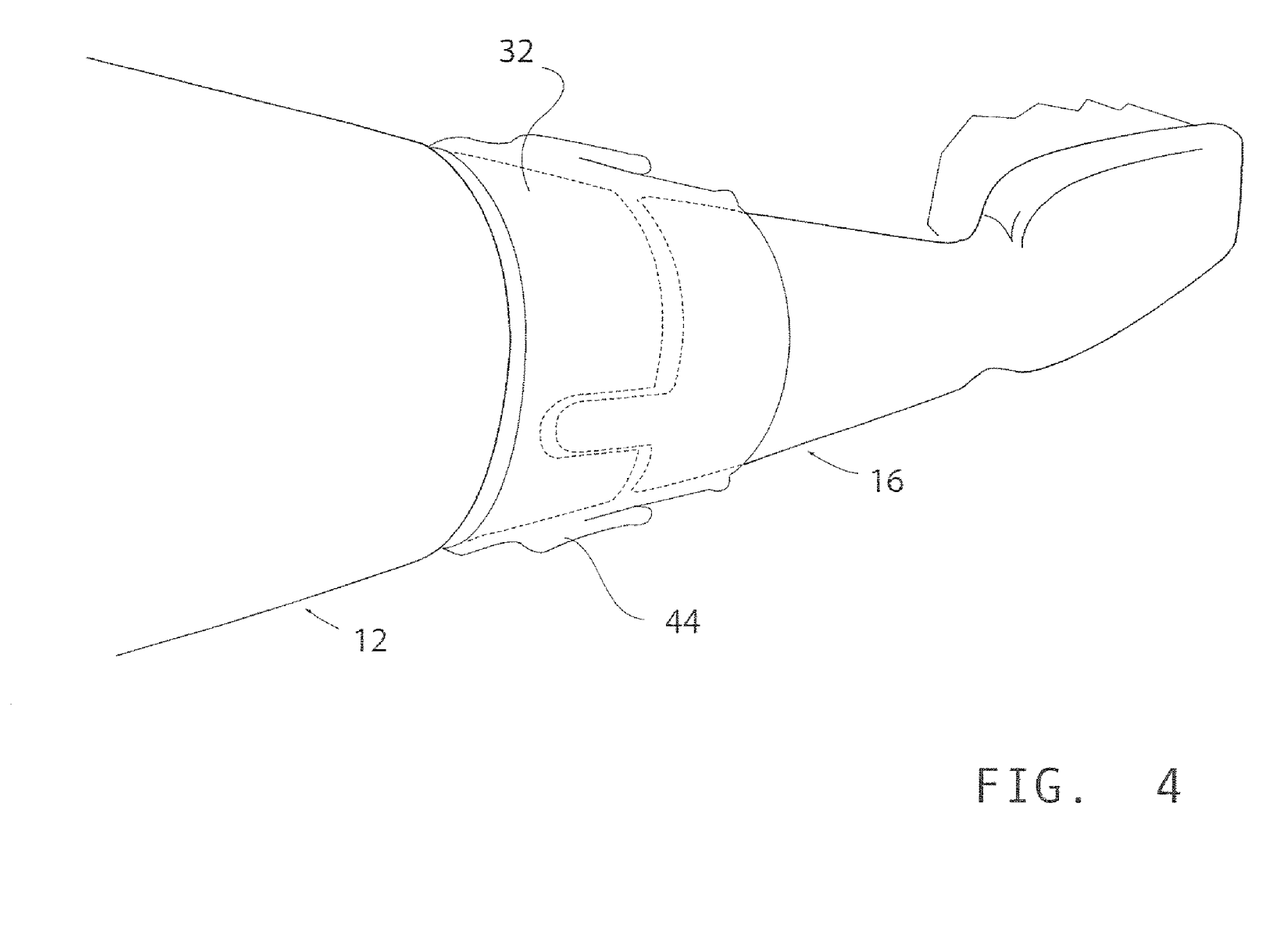
FIG. 4 is a perspective view showing an elastic cover sleeve.

FIG. 4 shows that the electric toothbrush 10 further comprises an elastic cover sleeve 44 that covers the selection sleeve 32 and part of the head body 16 that is adjacent to the selection sleeve 32.

Figure 2A:
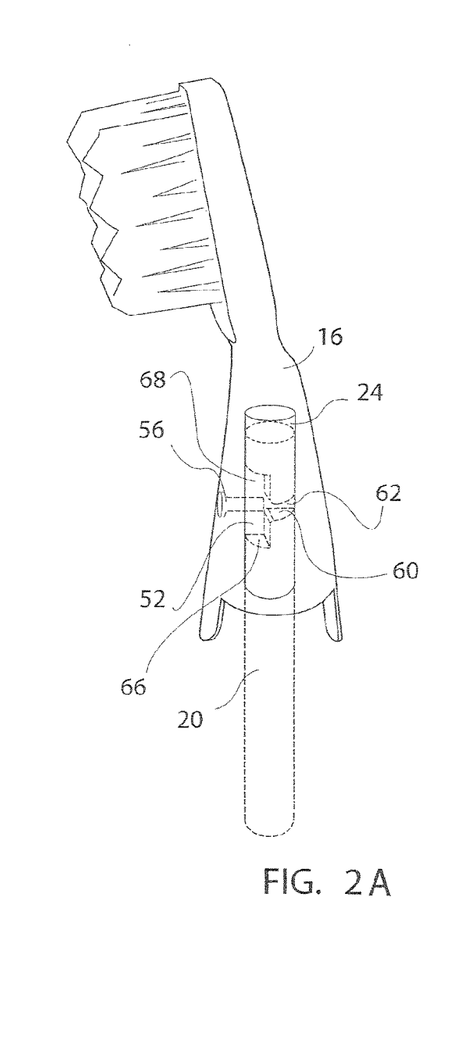
FIG. 2A is an elevation view of a brush head that is in penetration mode.
Figure 2B:
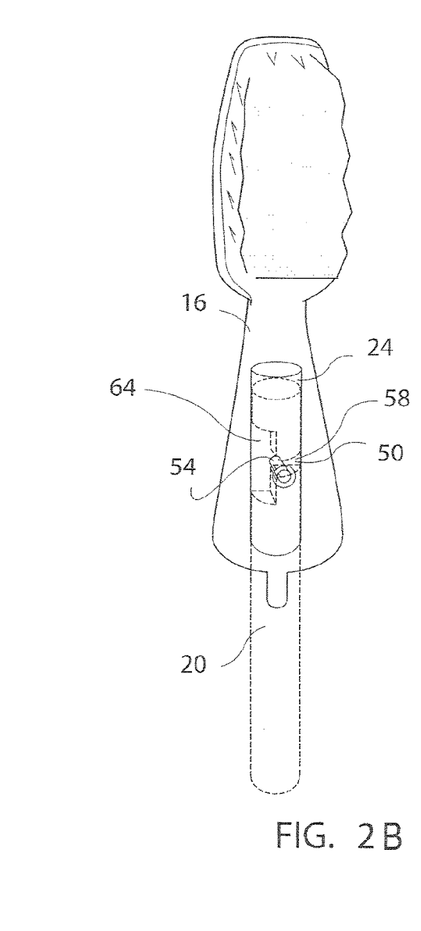
FIG. 2B is an elevation view of the brush head that is in polishing mode.

FIGS. 2A and 2B show that the reciprocating bar 20 comprises a lock recess 50 and a penetration recess 52. The engaging device 26 comprises a lock element 54 that engages with the lock recess 50 in the polishing mode, and that is allowed to move within the penetration recess 52. The lock element 54 has a dimension that fits the lock recess 50. The penetration recess 52 has a dimension that allows movement of the lock element 54 by the predetermined distance of the penetrating mode.

The lock element 54 comprises a circular pin 56 that is positioned perpendicular to the reciprocating bar 20. The lock recess 50 comprises a lock recess cut portion 58 that is cut into the reciprocating bar 20 perpendicular to the longitudinal axis of the reciprocating bar 20, two parallel lock recess walls 60 that have quarter circle shape and a flat lock recess bottom 62 that connects the two lock recess walls 60. The penetration recess 52 comprises a penetration recess cut portion 64 that is cut into the reciprocating bar 20 perpendicular to the longitudinal axis of the reciprocating bar 20, two parallel penetration recess walls 66 that have quarter circle shape and a flat penetration recess bottom 68 that connects the two penetration recess walls 66. The lock recess bottom 62 and the penetration recess bottom 68 are in the same plane.

Figure 5:
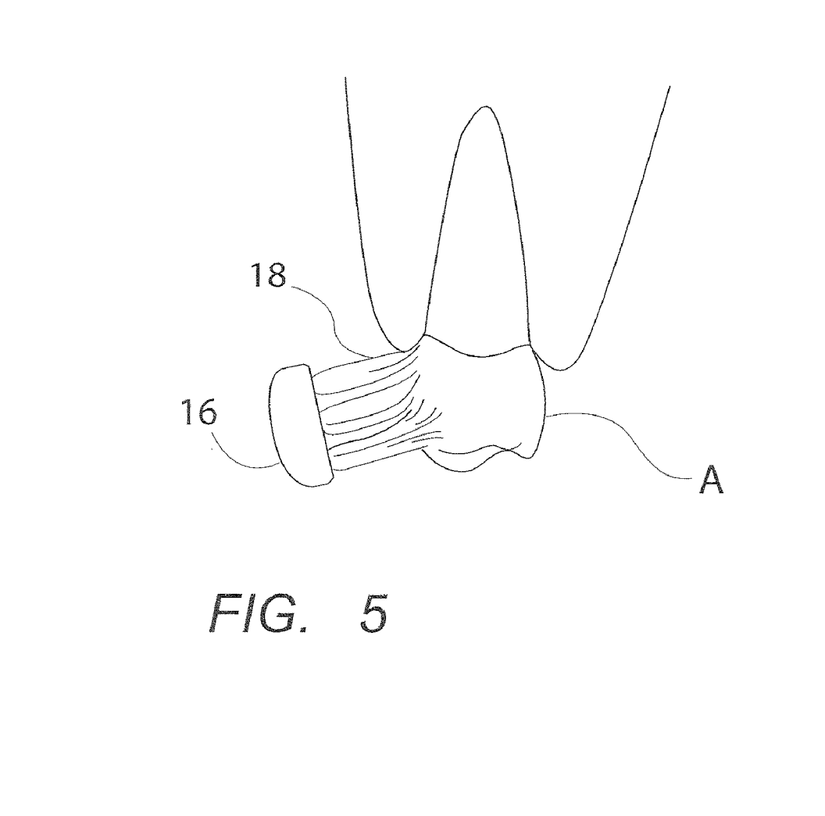
FIG. 5 is a schematic view showing how the bristles of the electric tooth brush are operated on a tooth and a gum surrounding the tooth.
Figure 6:
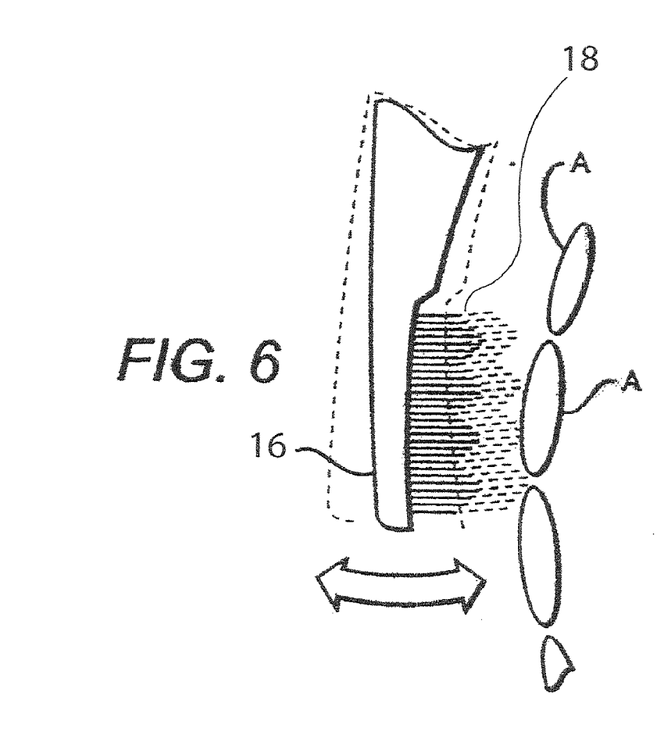
FIG. 6 is a schematic view showing the movement of the brush head in the penetration mode.

FIGS. 5 and 6 show how the bristles act on the teeth A in the penetration mode.

FIGS. 7A and 7B show that the actuator 22 comprises a motor 70 and a cam device 72. The cam device 72 converts rotational movement of the motor 70 into reciprocal movement of the reciprocating bar 20.

As shown in FIG. 7A, the brush head 14 is moved back to-and-fro substantially perpendicular to the longitudinal y-axis of the brush head 14 with an emphasis that it moves along the x-plane with the bristle tips pointing in the x-axis, and is moved back and forth parallel to the longitudinal y-axis of the brush head 14 simultaneously in the penetration mode. The simultaneous movements are required to prevent damage of the gum during the penetrating movement of the bristles 18.

As shown in FIG. 7B, the brush head 14 is moved side-to-side substantially perpendicular to the longitudinal y-axis of the brush head 14 with an emphasis that it moves along the x-plane with the bristle tips pointing in the z-axis, and is moved back and forth substantially parallel to the longitudinal y-axis of the brush head 14 simultaneously in the polishing mode.

As shown by the size of the arrows, the displacement of parallel movement of the brush head 14 in the penetration mode in FIG. 7A is smaller than the displacement of the parallel movement of the brush head 14 in the polishing mode in FIG. 7B.

The parallel movement of the brush head 14 in the penetration mode is caused by friction between the reciprocating bar 20 and the actuator receiving recess 24. The to-and-fro movement of the brush head 14 in the x-plane in the penetration mode is caused by the inherent oscillatory motion of the reciprocating bar 20 driven through the guide at the open end of the connecting sleeve 30 by the offset cam mechanism 72.

Referring back to FIG. 3, the electric toothbrush 10 further includes an elastic rubber ring 74 that is provided at the nose or guide of the handle 12 and controls the locomotive movement of the reciprocating bar 20, lateral movement of the reciprocating bar 20 induced by the offset cam is managed by the rubber ring in place at the guide. This elastic control of the reciprocating bar 20 reduces the lateral motion to a degree that results in controlled penetrating impulses to the gum in the penetrating mode. The elastic ring 74 is installed on the open end of the connecting sleeve 30 and contacts the brush head 14.

Action of plate cam with a follower rod fixed to an offset point on disk, creates output motion of both translational and oscillatory motion at the opposite end of the follower that is aligned along a longitudinal axis (6.1.1 Last sentence in paragraph.) The follower, at its midpoint, slides through a guide at the nose of the body, or handle, which encases the motorized cam mechanism. The output motion can be described in the following two ways: The relative midpoint of the follower moves through a rubber ring guide, which lines the nose of the body, in translational (up and down) motion, which directly follows the rotational motion of the cam. The follower, at its vertical tip, also sees oscillatory (back and forth, or chopping) motion that is reciprocal to the rotational motion of the cam; the follower behaves as a planar rocker through guide (5.1.2 Functions of Linkages.)

A section near the vertical tip of the follower rod is cut with two distinct grooves on two adjacent quarter sides of the rod. First quarter of the rod is cut with a female groove that mates with a fixed male screw that protrudes into the cylindrical hollow within the body of the brush-head. In this position (A), the brush-head locks into the mated groove of the follower rod. The adjacent quarter of the rod is cut with a longitudinally elongated female groove in where the male screw is free to move or slide longitudinally along the length of this elongated groove. In this position (B), the follower rod is free to slide within (the cylindrical hollow inside) the body of the brush-head, only limited by the predetermined length of the female groove, which allows the male screw movement. The latter position (B) creates independent, however limited, movement, or play, in the longitudinal or translational motion between the follower rod and the brush-head.

In the locked position (A), the orientation of the bristles on the brush-head stands perpendicular to the oscillatory output motion thereby utilizing primarily the translational output motion of the follower and creating a sweeping, or polishing effect in one plane in respect to the contact point, or face, of the bristles. In position B, the orientation of the bristles is, or stands, in-line with the oscillatory output motion thereby following this to-and-fro motion that creates a chopping or digging movement that is multi-planar in respect to the contact point of the bristles.

In this position (B), the oscillatory motion of the bristles is coupled with the freely sliding effect between the body of the brush-head and the follower, allowing for variable translational position of the brush-head that creates a virtual suspended state, or floating of the brush-head in midair as the cam rotates at high frequency. With this slight, but variable instantaneous positioning of the brush-head from the high velocity in oscillatory and translational motion (with play), the bristles achieve a digging effect that can instantaneously conform to minute changes in contact surface; thus ultimately producing thorough penetrating effect deep within the gumline.

Unlike all other mechanical devices that have fixed linkages that rigidly follow the rotation of a driving mechanism, this invention harnesses a free, variable movement within its mechanics to achieve an organic element to its output motion. This element of the invention is critical to effective bristle placement for complete hygiene by adapting to the organic form and minute spaces that constitutes most critical and important areas of the tooth and gum.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. An electric toothbrush comprising:
   a) a handle;
   b) a brush head comprising a head body and a plurality of bristles fixed to the head body;
   c) a reciprocating bar provided inside the handle;
   d) an actuator that moves the reciprocating bar back and forth;
   e) an actuator receiving recess provided inside the head body of the brush head, wherein the reciprocating bar is protruded from the handle and received in the actuator receiving recess;
   f) an engaging device that engages the brush head with the reciprocating bar so that the brush head moves relative to the reciprocating bar in either penetration mode or polishing mode; and
   g) a selection device that places the engaging device either in the penetration mode or the polishing mode;
   h) an electric power source;
   wherein the brush head moves together with the reciprocating bar in the polishing mode, wherein the brush head is free to move relative to the reciprocating bar within a predetermined distance in the penetration mode, wherein the longitudinal axis of the brush head is inclined from the longitudinal axis of the handle with a predetermined angle,
   wherein the handle comprises a connecting sleeve that is provided on the end of the handle that is adjacent to the brush head, wherein the selection device comprises:
      a) a selection sleeve that is provided between the handle and the brush head and surrounds the connecting sleeve;
      b) a selection protrusion that is provided inside the selection sleeve; and
      c) a selection groove that is provided on the connecting sleeve and receives the selection protrusion;
   wherein the selection groove comprises two angularly spaced mode recesses that keep the selection protrusion either in the polishing mode or the penetration mode.

2. The electric toothbrush of claim 1, wherein the mode recesses are spaced by about 90 degrees.

3. The electric toothbrush of claim 1, further comprising an elastic cover sleeve that covers the selection sleeve and part of the brush head that is adjacent to the selection sleeve.

4. The electric toothbrush of claim 1, wherein the selection sleeve comprises a guide groove and the head body of the brush head comprises a guide bar that is received in the guide groove and moves along the guide groove.

5. The electric toothbrush of claim 1, wherein the reciprocating bar comprises a lock recess and a penetration recess, wherein the engaging device comprises a lock element that engages with the lock recess in the polishing mode, and that is allowed to move within the penetration recess, wherein the lock element has a dimension that fits the lock recess, wherein the penetration recess has a dimension that allows movement of the lock element by the predetermined distance of the penetrating mode.

6. The electric toothbrush of claim 5, wherein the lock element comprises a circular pin that is positioned perpendicular to the reciprocating bar, wherein the lock recess comprises a lock recess cut portion that is cut into the reciprocating bar perpendicular to the longitudinal axis of the reciprocating bar, two parallel lock recess walls that have quarter circle shape and a flat lock recess bottom that connects the two lock recess walls, wherein the penetration recess comprises a penetration recess cut portion that is cut into the reciprocating bar perpendicular to the longitudinal axis of the reciprocating bar, two parallel penetration recess walls that have quarter circle shape and a flat penetration recess bottom that connects the two penetration recess walls, wherein the lock recess bottom and the penetration recess bottom are in the same plane.

7. The electric toothbrush of claim 1, further comprising an elastic ring that is in installed on the open end of the connecting sleeve and contacts the brush head, which controls the amount of vibration and pressure exerted on the brush head from the reciprocal movement of the reciprocating bar.

* * * * *